United States Patent [19]

Morra

[11] Patent Number: 5,792,194
[45] Date of Patent: Aug. 11, 1998

[54] TRANSVALVULAR IMPEDENCE MEASUREMENT

[75] Inventor: Antonio Morra, Salzano, Italy

[73] Assignee: Medico SpA, itx

[21] Appl. No.: 721,187

[22] Filed: Sep. 27, 1996

[30] Foreign Application Priority Data

Sep. 29, 1995 [IT] Italy .................. TO95 A 000777

[51] Int. Cl.$^6$ .................. A61N 1/05; A61N 1/06
[52] U.S. Cl. .................. 607/17; 607/28; 607/122
[58] Field of Search .................. 607/4, 7, 8, 17, 607/27, 28, 122, 123

[56] References Cited

U.S. PATENT DOCUMENTS

| | | |
|---|---|---|
| 4,184,493 | 1/1980 | Langer . |
| 4,202,340 | 5/1980 | Langer . |
| 4,303,075 | 12/1981 | Heilman . |
| 4,444,195 | 4/1984 | Gold .................. 607/122 |
| 4,702,253 | 10/1987 | Nappholz . |
| 4,773,401 | 9/1988 | Citak et al. . |
| 4,805,621 | 2/1989 | Heinze et al. .................. 607/17 |
| 5,003,975 | 4/1991 | Hafelfinger et al. .................. 607/28 |
| 5,215,081 | 6/1993 | Ostroff .................. 607/8 |
| 5,314,449 | 5/1994 | Lindgren .................. 607/24 |
| 5,562,711 | 10/1996 | Yerich et al. .................. 607/17 |
| 5,603,725 | 2/1997 | Schaldach . |
| 5,626,624 | 5/1997 | Schaldach et al. . |

FOREIGN PATENT DOCUMENTS

| | | |
|---|---|---|
| 0 557 550 | 9/1993 | European Pat. Off. ........ A61N 1/368 |
| 41548A/86 | 3/1986 | Italy . |
| 945058 | 5/1991 | Italy . |
| 1 567 025 | 5/1980 | United Kingdom .......... A61N 1/04 |
| 2 070 282 | 9/1981 | United Kingdom .......... A61N 1/36 |
| 91/06512 | 3/1994 | WIPO .......... A61N 1/365 |

OTHER PUBLICATIONS

Alan D. Bernstein, et al., "The NASPE*/BPEG**Generic Pacemaker Code for Antibrafyarrhythmia and Adaptive-Rate Pacing and Antiachyarrhythmia Devices", *Pace*, vol. 10, pp. 794–799, (Jul.–Aug. 1987).

Raul Chirife, et al., "Feasibility of Measuring Relative Right Ventricular Volumes and Ejection Fraction with Implantable Rhythm Control Devices", *Pace*, vol. 16, pp. 1673–1683, (Aug. 1993).

Mark Harvey, et al., "Impedance Monitoring During Radiofrequency Catheter Ablation in Humans", *Pace*, vol. 15, pp. 22–27, (Jan. 1992).

Ilya Ovsyshcher, et al., "Precision of Impedance Cardiography Measurements fo Cardiac Output in Pacemaker Patients", *Pace*, vol. 15, pp. 1923–1926, (Nov. Part II 1992).

Hetty J. Wortel, et al., "Impedance Measurements in the Human Right Ventricle Using a New Pacing System", *Pace*, vol. 14, pp. 1336–1342, (Sep. 1991).

Dirar Khoury, et al., "Continous Right Ventricular Volume Assessment by Catheter Measurement of Impedance for Antitachycardia System Control", *Pace*, vol. 12, pp. 1918–1926, (Dec. 1989).

Tibor Nappholtz, et al., "Electrode Configuration for a Respiratory Impedance Measurement Suitable for Rate Responsive Pacing", *Pace*, vol. 9, pp. 960–964, (Nov.–Dec. 1986).

John C. Woodard, et al., "Right Ventricular Volumentry by Catheter Measurement of conductance", *Pace*, vol. 10, pp. 862–870, (Jul.–Aug. 1987).

(List continued on next page.)

*Primary Examiner*—George Manuel
*Assistant Examiner*—Carl H. Layno
*Attorney, Agent, or Firm*—Beck & Tysver

[57] ABSTRACT

A transvalvular impedance measurement made between an atrium and a ventricle electrode of a standard implanted electro-catheter may be used to provide information indicative of the mechanical state of the heart. This information may be used, for example, to control the pacing rate of a rate responsive pacemaker, stimulation intensity self adjust or pacing mode switching. Other uses are also possible in defibrillators.

33 Claims, 12 Drawing Sheets

OTHER PUBLICATIONS

Ilya Ovsyscher, et al., "Impedance Cariography for Cardiac Output Estimation in Pacemaker Patients", *Pace*, vol. 16, pp. 1412–1422, (Jul. 1993).

E. Alt, et al., "Feasibility of Using Intracardiac Impedence Measurements for Capture Detection", *Pace*, vol. 15, pp. 1873–1879, (Nov. 1992).

Tommaso Scalise, et al., "Discussion of A Proposed Biophysical Model For Atrial Floating Sensing Leads", *Medico*, 2nd International Symposium on Pacing Leads, pp. 1–9, (1991).

Giuseppe Curzio, "A Multicenter Evaluation of a Single-Pass Lead VDD Pacing System", *Pace*, vol. 14, No. 3, pp. 434–442, (Mar. 1991).

"Results of Eight Years of VDD Single Lead Stimulation", Medico Satellite Symposium, pp. 1–30, (Jun. 6–9 1993).

"Phymos 830–S, Phymos 935 and Adakit", Procedural Manual, pp. 23–39, (1994).

"Phymos 3D (DDD/VDD–M)", Procedural Manual, pp. 50–95, (1994).

TRANSVALVULAR IMPEDENCE MEASUREMENT

FIELD OF THE INVENTION

The invention relates to methods and apparatus for determining the mechanical state of the heart generally, although not exclusively, the human heart. This invention also relates to methods and apparatus for controlling the functioning of a heart in accordance with information obtained about its mechanical state.

BACKGROUND

Information about the mechanical functioning of a heart can be obtained by a physician by use of a stethoscope to listen to the heart. Also, electrical signals produced by the heart can be used to check its functioning. Thus, in a healthy heart the sinus node, situated in the right atrium, generates electrical signals which propagate throughout the heart and control its mechanical movement. The detection of this electrical signal and its relationship to the mechanical state of the heart are well known. Suitably processed this electrical information can be used for diagnostic purposes by display, for example, on an electrocardiograph.

Common problems with the heart are that the electrical signal, although correctly generated, is not propagated correctly. This can be cured by a conventional pacemaker which detects the electrical signal and artificially paces the required parts of the heart. The sinus node activity is detected by an electrode and used to trigger (with suitable time delays) electronic stimulus (pacing) of the atrium and/or ventricle depending upon the requirements of the patient and the set up of the pacemaker.

Another problem is that the heart may go into a fibrillation state. Again the above electrical signal may often be used in the control of defibrillators.

Some medical conditions, however, affect the relationship between the electrical and mechanical activity of the heart and, therefore, measurement of electrical activity only cannot be relied upon as indicative of the true status of the heart or as suitable for triggering stimulation of the heart. Furthermore other medical conditions result in the absence of any detectable electrical signal.

In the above example, this problem means that pacing cannot be performed as described above and conventionally is instead performed at a fixed rate. The disadvantage of such an approach is that, as is known, the heart must be ideally be paced at different rates depending upon the metabolic state of the patient. The above approach does not allow for this, resulting in overpacing at times of low need (e.g. whilst sleeping) and underpacing at high need (e.g. during exercise).

In order to solve the problem of the above example the use of rate responsive pacemakers has been proposed. In such pacemakers, pacing is performed at a frequency at least partly determined by an external, metabolically influenced, variable. Various external variables have been proposed, for example a motion detector to measure the motion of the patient. However such solutions can only be a compromise as the correlation between conventionally measured external variables and metabolic rate is not ideal. In the example of the motion detector the device cannot differentiate between the patient's own movement and that externally produced (such as when the patient is riding in a vehicle.)

Various other measurements suitable for control of rate responsive pacing have been proposed. In "Electrode Configurations for Respiratory Impedance Measurements Suitable for Rate Responsive Pacing" by T Nappholtz, H Valenta, Maloney and Simmons published at page 960 of PACE Volume 9 (November/December 1986, Part II) it is proposed that certain electrical impedance (hereinafter referred to as impedance) measurements would give a measure of respiration in circumstances where the impedance was measured across the lungs. A particular solution is proposed whereby measurements are taken using conventional pacing leads and the impedance between one or more electrodes of the pacing lead and the pacemaker case was measured, this path being predominantly across a lung. A similar proposal is made in "Right Ventricular Volumetry by Catheter Measurement of Conductance" by J Woodard, C Bertram and B Gow at page 862 PACE Volume 10 (July/August 1987, Part I).

The measurement of intracardiac impedance (either in the ventricle or the atrium) is proposed in "Feasibility of Using Intracardiac Impedance Measurements for Capture Detection" by E Alt, C Kriegler, P Fotuhi, R Willhaus, W Combs, M Heinz and D Hayes at page 1873 PACE Volume 15, (November 1992, Part II). Impedance measurements are taken between electrodes positioned in the same chamber of the heart, such measurements indicative of the speed of ejection of the blood from the ventricle.

SUMMARY OF THE INVENTION

In accordance with an aspect of the invention there is proposed use of at least one electro-catheter (pacing lead) having at least one electrode in each chamber of one side of a heart for producing a transvalvular impedance measurement.

An embodiment of the invention provides apparatus which allows measurement of the impedance across the tricuspid valve between the atrium and the ventricle of the right hand side of the heart. The inventors have determined that this impedance is indicative of the mechanical functioning of the heart, for example of the state of opening of the valve, and of various stages of atrium and ventricular expansions and contractions.

An embodiment of the invention provides apparatus for or a method of providing a signal suitable for the control of a heart stimulating device such as a pacemaker or defibrillator using information obtained from the impedance measured across the tricuspid valve.

An aspect of the present invention also provides a transvalvular impedance measurement signal for use in monitoring or controlling operation of the heart.

An embodiment of the present invention provides transvalvular impedance measuring means and means for determining a pacing rate for a heart pacing circuit in accordance with the following equation:

$$\text{pacing rate} = R_0 + K_1(T_{CYCLE}/T_1) + K_2(dZ/dT)$$

where $R_0$, $K_1$ and $K_2$ are determined by the characteristics of the heart to be paced;

$T_{CYCLE}$ is the period of cyclical variation of the transvalvular impedance signal, $T_1$ is the time between an impedance minimum and maximum, and $dZ/dT$ is the rate of change of the transvalvular impedance between the minimum and maximum.

BRIEF DESCRIPTION OF THE DRAWINGS

Embodiments of the present invention will now be described, by way of example only, with reference to the accompanying drawings in which.

DESCRIPTION OF THE PREFERRED EMBODIMENTS

Figure 1:
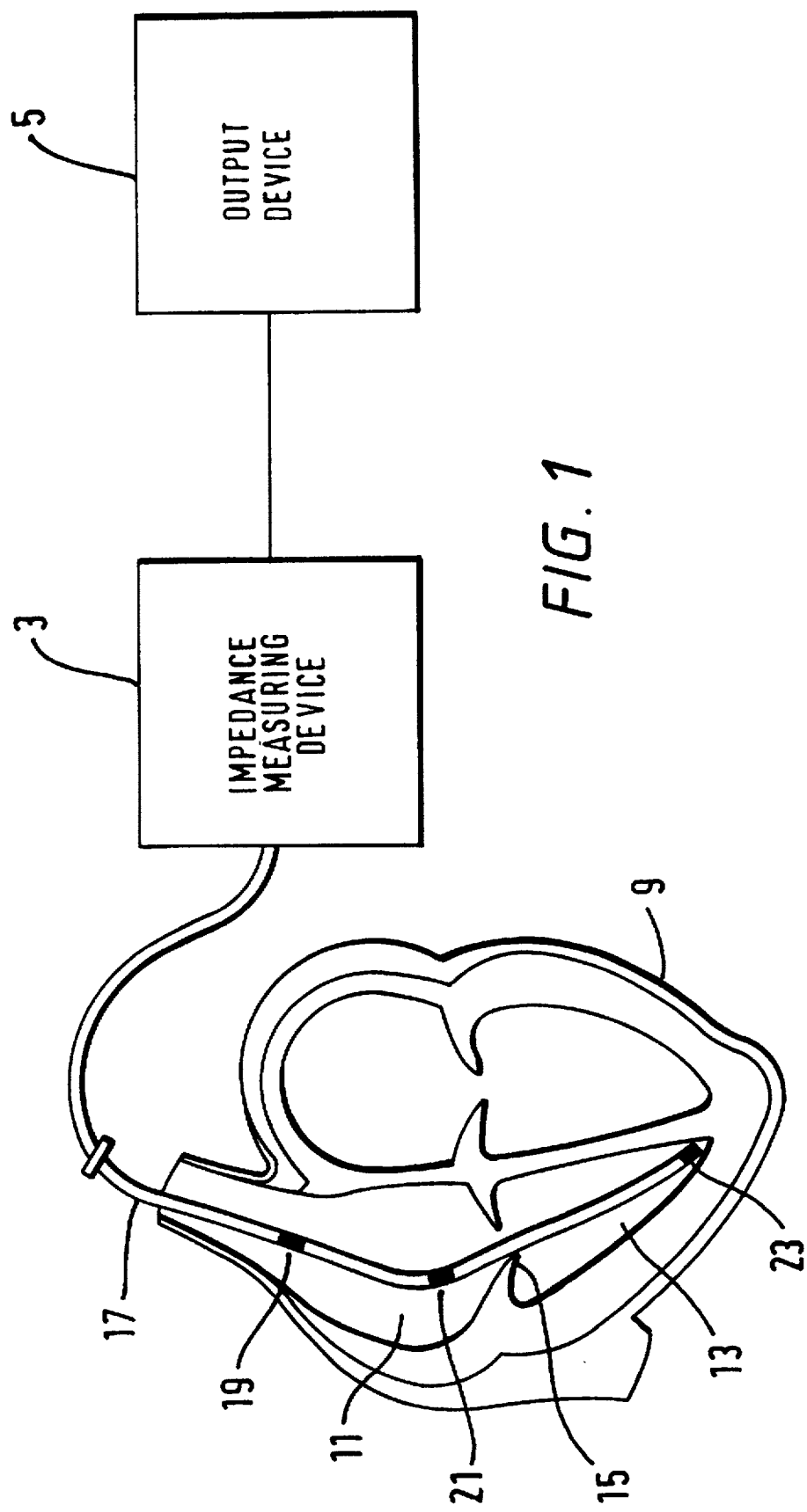
FIG. 1 is a schematic block diagram of apparatus embodying the present invention.

Referring now to FIG. 1, an electro-catheter is shown as having been surgically placed so as to extend through the right atrium 11 across the tricuspid valve 15 and into the right ventricle 13 of the heart 9 of a patient (not shown), so as to have at least one electrode situated in the atrium 11 and at least one electrode situated in the ventricle 13. The insertion process is well-known and will not be described in any greater detail. The ventricle electrode 23 is suitably positioned adjacent to the wall of the ventricle 13 and may be retained in that position by the barbs 37 shown in FIG. 3 hereof. Atrium electrodes 19 and 21 are positioned in the atrium cavity 11 away from the atrium wall and retain a limited degree of movement. The electro-catheter 17 may have previously been implanted for use with a pacemaker or defibrillator, for example.

Wirings (not shown in FIG. 1) extending through the electro-catheter 17 couple each of the electrodes 19, 21, 23 to respective electrical connection pins (not shown in FIG. 1).

An impedance measurement across the tricuspid valve 15 is made between an atrium and a ventricle electrode by coupling those to an impedance measuring device 3, examples of which will be described below. An impedance Z measured by the impedance measuring device 3 may be supplied to an output device 5 such as a chart recorder, display screen or to a computer for further processing.

Alternatively or additionally, the measured impedance Z may be supplied to a control device for controlling operation of the heart.

Figure 2:
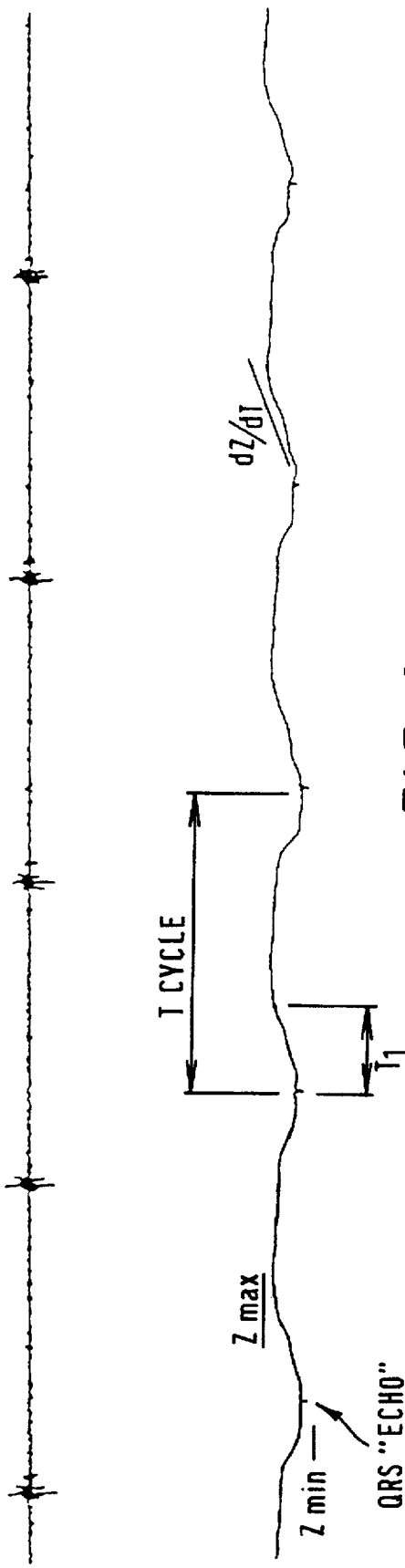
FIG. 2a shows the output of an electrocardiograph and FIG. 2b shows output data produced by a chart recorder coupled to the impedance measuring apparatus shown in FIG. 1, when connected to a patient.

FIG. 2b illustrates a graph of impedance Z against time t, showing the results of an impedance measurement made in the manner described above. For comparison FIG. 2a shows the "A" wave from a contemporaneous output from an electrocardiograph (ECG). The inventor has determined that the measured impedance Z changes with time in response to the mechanical operation of the heart, in particular in response to the opening and closing of the tricuspid valve and that the measured impedance and the manner in which it changes with time can be used to monitor or control aspects of the operation of the heart, examples of which will be described below.

As shown in FIG. 2b, the measured impedance varies cyclically with time and the inventor has determined that the cycle time $T_{cycle}$ is dependant upon the period or cycle time of the heart and therefore the heart beat rate. $T_{cycle}$ may therefore be used to monitor or control the heart beat rate.

The inventor has also determined that the maximum measured impedance $Z_{MAX}$ is indicative of the tricuspid valve being closed and that the minimum measured impedance $Z_{MIN}$ is indicative of the tricuspid valve being open. The time of occurrence of $Z_{MIN}$ and $Z_{MAX}$ may be used to determine the responsiveness of the heart to an external stimulus, for example that applied by a pacemaker.

The inventor has also identified that the time $T_1$ from an impedance minima $Z_{MIN}$ to the following impedance maxima $Z_{MAX}$ corresponds to the time that the valve takes to close and is inversely proportional to the speed of the contraction of the ventricle 13. The speed of contraction is indicative of the metabolic needs of the patient. The time $T_1$ can therefore be used to provide an indication of the metabolic needs of the patient and may be used, for example to control the rate of an externally applied stimulus such as from a pacemaker or to monitor the response of the patient's heart to physical exertion. Further aspects of the significance of time period $T_1$ are discussed below in relation to FIG. 10.

The inventor has further identified that the average rate of change of impedance during the period $T_1$ (dZ/dT), that is to say during valve closure, provides an indication of the cardiac muscle contractivity and thus of the physical exertion of the patient.

An example of one way in which an impedance measurement in accordance with the invention may be made will now be described with reference to FIGS. 3 to 5.

Figure 3:
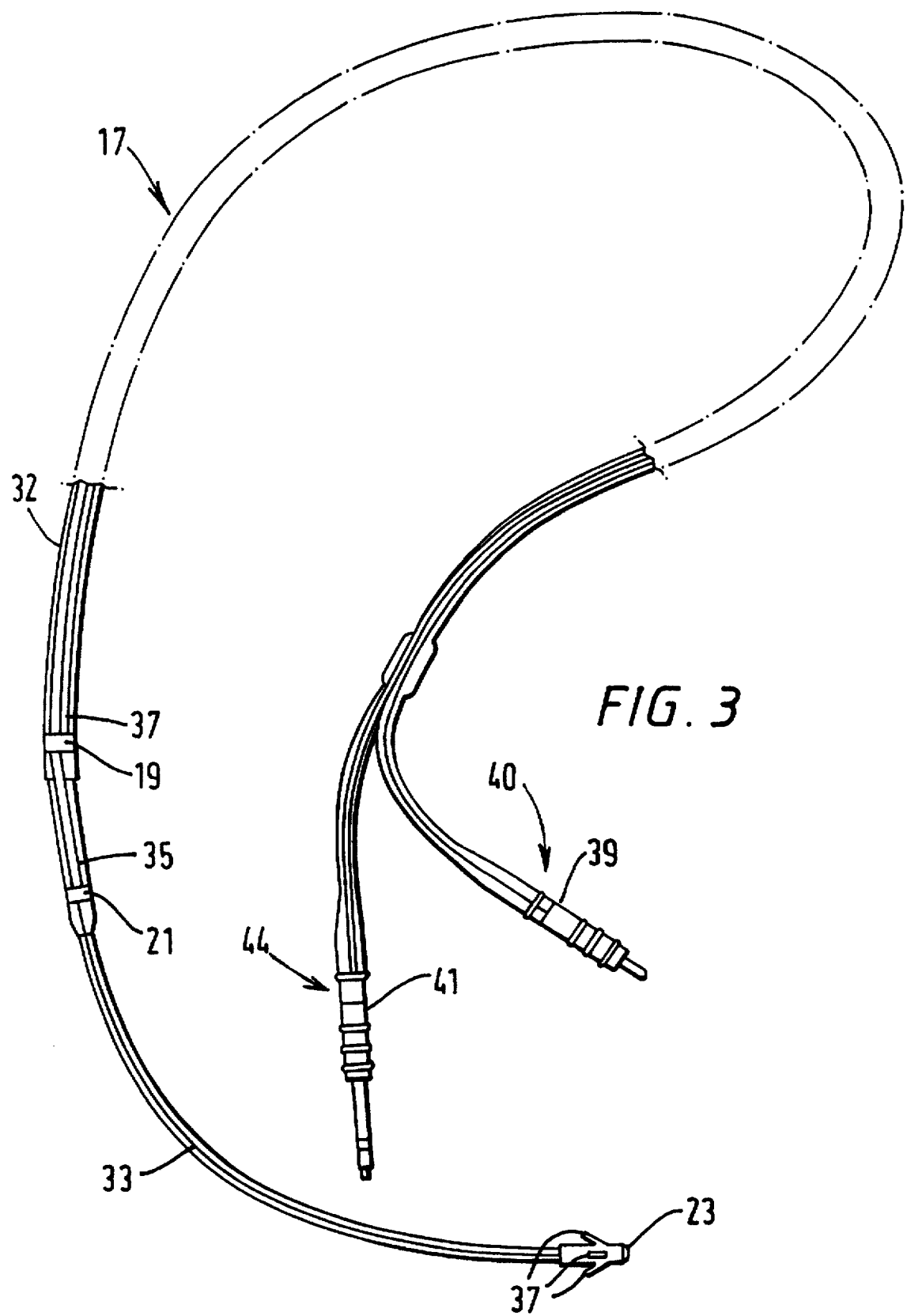
FIG. 3 schematically shows a typical pacing lead of the dual atrial/single ventricle electrode type.

FIG. 3 shows in detail one example of an electro-catheter 17 designed for use with a pacemaker and suitable for use in making an impedance measurement. The electro-catheter 17 comprises a flexible insulative, generally silicone, tubular sleeve or body 32 with a ventricle electrode 23 at one end, adjacent to which are small barbs 37. Spaced along the lead are an atrium distal electrode 21 and an atrium proximal electrode 19. The other end of the lead splits into two sections 40, 44 each terminating in an electrical connection pin 39, 41.

Pin 39 has one electrical terminal connected by internal wiring 33 to the ventricular electrode 23. Pin 41 has two electrical terminals connected by internal wirings 35, 37 to the two atrium electrodes 19, 21 respectively. The two pins 39, 41 which would normally be coupled to the pacemaker, can be coupled to the impedance measuring device 3 to enable an impedance measurement to be made between one of the atrium electrodes 21, 19 and the ventricle electrode 23.

The body 32 of the electro-catheter 17 is typically 68 cm (centimeters) in length and of a maximum diameter 3.5 mm (millimeters). The electrodes 23, 21, 19 are typically constructed from Platinum-Iridium 90/10. The ventricle electrode 23 is typically hemispherical in shape and is of typical maximum diameter 2.6 mm, surface area 6.6 mm² and electrical resistance 31 ohms. The atrium electrodes 19 and 21 are cylindrical in shape, their longitudinal axes being the same as that of the body 32. Both electrodes are typically 15.8 mm² in area and of electrical resistance 61 ohms. Typically the spacing between the ventricle electrode 23 and atrium distal electrode 21 is 13 cm and the distance between the two atrium electrodes is 3 cm, although leads are commonly available in a variety of alternative electrode spacings.

An electro-catheter of the type shown in FIG. 3 is described in detail in Italian Patent specification IT 41548/86, and is commercially available from Medico Spa under item number MOD 830-S.

Examples of the impedance measuring device 3 will now be explained more fully with reference to FIGS. 4 and 5.

Figure 4:
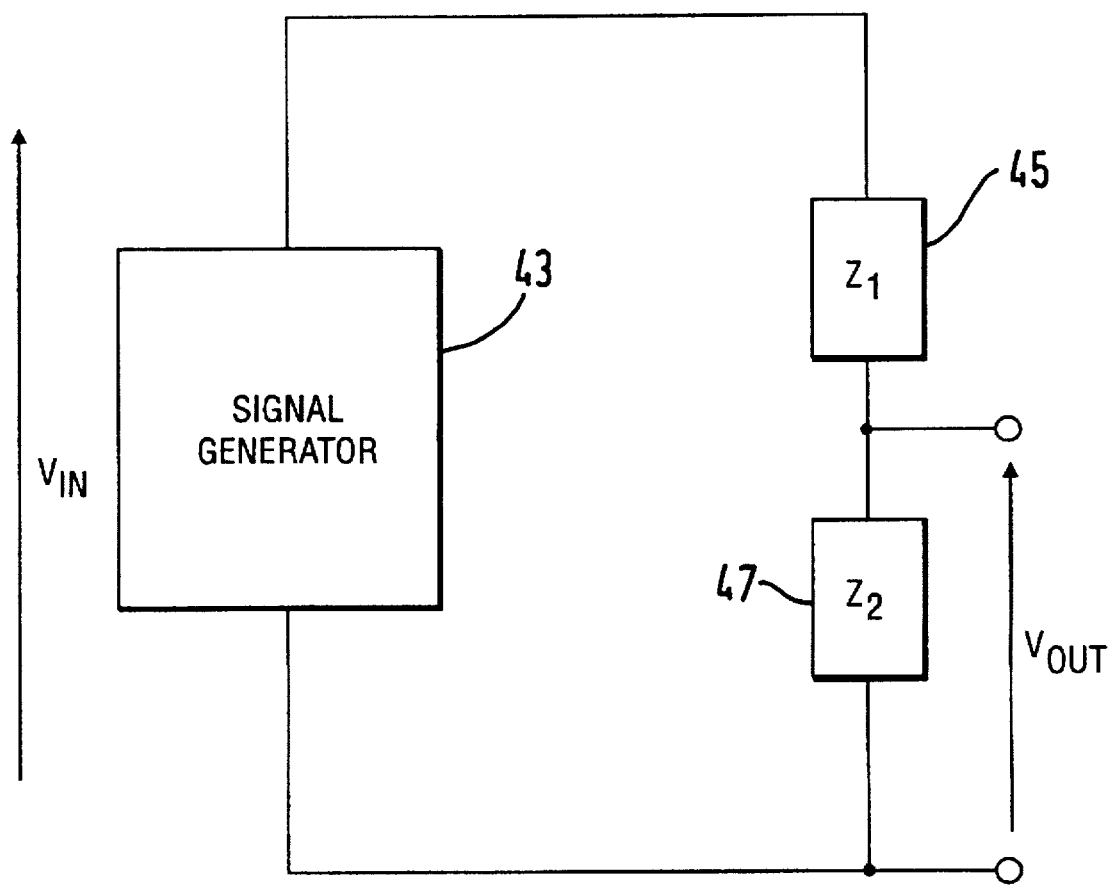
FIG. 4 shows a schematic circuit diagram of a bridge circuit suitable for the measurement of transvalvular impedance in an impedance measuring apparatus embodying the invention.

As shown in FIG. 4 the measuring device 3 may comprise a potential divider or bridge network and a signal generator 43 for applying a voltage $V_{IN}$ across the combination of known value impedance $Z_1$ (45) and the transvalvular impedance to be measured, $Z_2$ (47). Known value impedance $Z_1$ is preferably provided by a known value resistor and a known value capacitor connected together in series. The voltage $V_{OUT}$ which occurs across the tricuspid valve is then measured by a suitable device, an example of which is described hereinbelow. As $V_{IN}$ and $Z_1$ are known and $V_{OUT}$ is measured, $Z_2$ can thus be calculated by applying the well known formula:

$$Z_2 = \frac{V_{OUT}}{V_{IN} - V_{OUT}} Z_1$$

Figure 5:
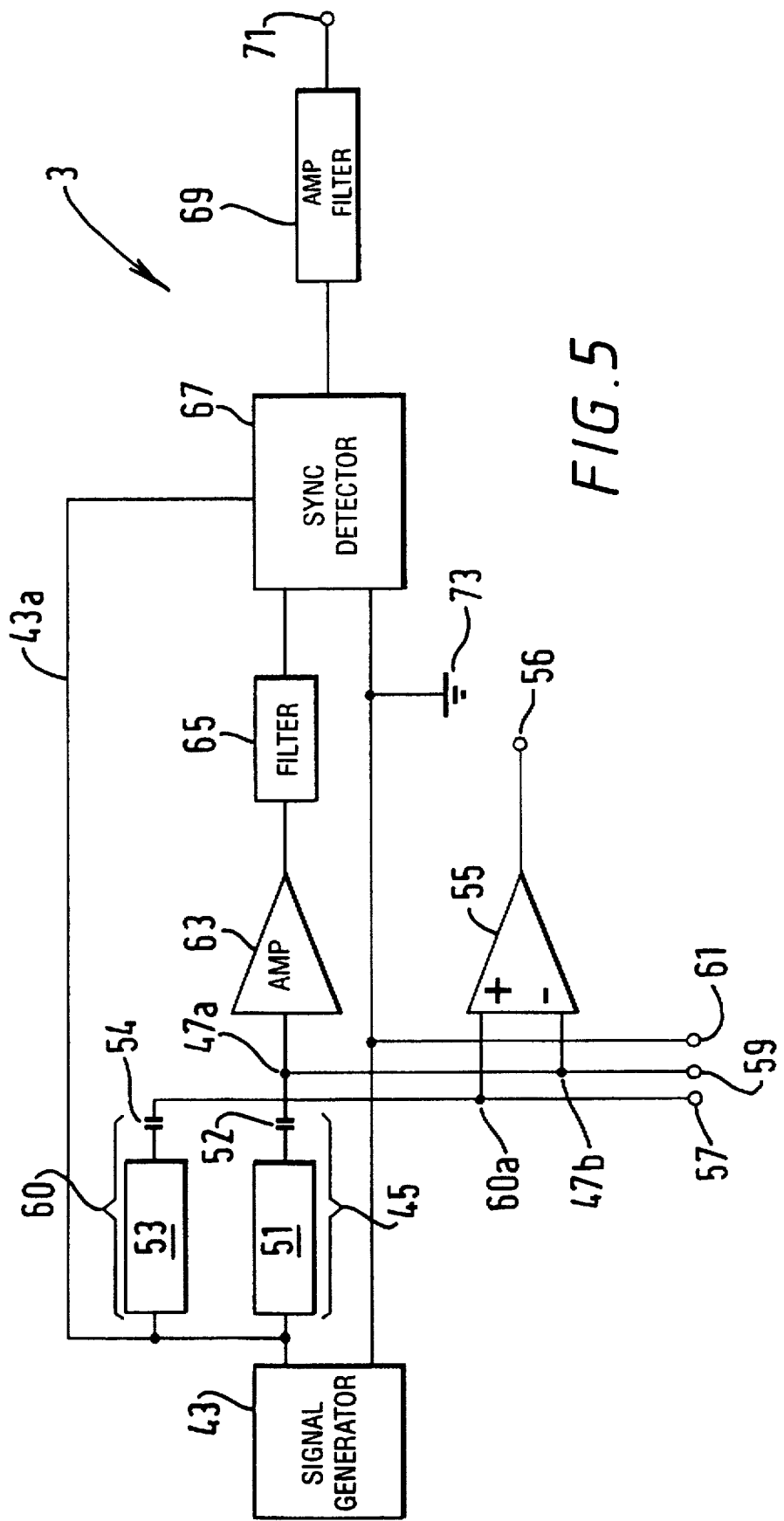
FIG. 5 shows a schematic block diagram of a first example of an impedance measuring apparatus embodying the invention.

FIG. 5 is a schematic block diagram of an impedance measuring device 3 in which the known impedance $Z_1$ of FIG. 4 is provided by a first network 45 comprising series-connected resistor 51 and capacitor 52. The signal generator 43 output is also coupled to a second network 60 comprising series-connected resistor 53 and capacitor 54. Signal generator output is relative to ground 73. Resistors 51 and 53 are of identical value as are capacitors 52, 54. First network 45 is coupled via node 47a to atrium distal connection pin 59 so as to form a potential divider with the impedance $Z_2$ to be measured. The node 47a is also coupled to the input of an amplifier 63. The second network is coupled to the atrium proximal connection pin 57. The first and second networks 45 and 60 are connected via nodes 47b and 60a to respective inputs of a differential amplifier 55, the output of which provides an atrium sense output 56. The output of amplifier 63 is connected to the input of a filter 65, the output of which is thereafter connected to the input of synchronous detector 67. The synchronous detector 67 is synchronised by the output of signal generator 43 which is supplied via line 43a. The output of synchronous detector 67 is connected to the input of an amplifier/filter combination 69 whose output is thereafter available at output 71. Ventricle connection pin 61 is connected to ground 73.

In use of the impedance measurement device 3 shown in FIG. 5 to measure a transvalvular impedance, connection pins 57, 59, 61 are connected to the atrium proximal and distal terminal pin 41 and ventricle terminal pin 39 respectively of the electro-catheter 17 shown in FIG. 3.

Signal generator 43 generates a square wave of frequency 4 KHz, amplitude 3 volts. The signal generator is arranged so that its output voltage varies between 0 (earth/ground potential 73) and 3 volts.

It will be appreciated by a person skilled in the art that an alternating signal is necessary if one is to measure to reactive part of the impedance. In fact the impedance to be measured $Z_2$ is mostly resistive in nature. However, further advantages of using an alternating signal are that such a signal is considered to create less interference with the electrical activity of the heart. Furthermore, when the impedance measuring device is designed so as to be portable or implantable, power supply longevity is of consequence and an alternating or pulsed signal can be produced in such a manner that it consumes less power. The signal generator 43 may be a commercially available counter driven by a oscillator, although any other known suitable signal generating means could be used.

The impedance to be measured ($Z_2$) typically ranges between 100 to 1000 ohms. Preferably therefore, the current flow across the heart valve should be in the range 1 to 10 µA (microAmperes) as it is necessary to keep the current flow through the heart to a minimum for similar reasons to those given above for the use of alternating or pulsed voltage. This may be achieved by selecting the value of the resistor 51 to be between 10 and 1000 KΩ (Kilo-Ohms), preferably 330 KΩ and the value of the capacitor 52 to be between 10 and 50 nF (nanoFarads), preferably 22 nF.

In the example described above, the impedance $Z_2$, is measured by determining the potential difference between the ventricle electrode 23 and the distal rather than the proximal atrium electrode. This is because the inventor has determined that the impedance measurement between the distal atrium electrode 21 and the ventricle electrode 23 is more sensitive to the mechanical operation of the heart and exhibits proportionally a greater variation in impedance than that which would be produced using the proximal atrium electrode 19 because the distal atrium electrode 21 is closer to the ventricle electrode 23.

Connecting the output of the signal generator 43 to both of the impedance networks 45 (51,52) and 60 (53,54) and driving the atrium sense output 56 from differential amplifier 55 enables the electrical activity of the sinus node in the atrium to be detected even when a signal is being supplied by the signal generator 43 because the applied impedance measuring voltage is removed by connection of the two atrium sensing electrodes to the differential amplifier 55.

The voltage level at the distal atrium electrode pin 59 is thereafter amplified by amplifier 63 and filtered by filter network 65. The amplifier typically has a gain in region 50 to 200, preferably 100. Typically, the filter network comprises a notch filter to reject mains frequency (50 or 60 Hz (Hertz)) and also a low pass filter to reject frequencies exceeding 100 Hz, the frequencies of the signals of interest being well below this. In this way noise generated in impedance measurement can be reduced.

The output signal from the amplifier 63 is thereafter passed to a synchronous detector 67. As will be apparent, a meaningful output is only produced when the signal produced by the signal generator 43 is stable and non-zero. The synchronous detector passes the signal applied to its input through to its output upon the application of a positive control signal, which in this case is the signal generator output supplied on line 43a. When there is no signal supplied by the signal generator 43 on line 43a, the output of the synchronous detector is held at its former value. The synchronous detector may be embodied for example by a standard CMOS 4066 although any suitable switch or sample and hold device could be used. Preferably the synchronous detector, together with other components will be incorporated in a custom integrated circuit. Thereafter the signal is further amplified and filtered by amplifier/filter 69 to provide output 71 suitable for recording, display or control. For example, the output 71 may be supplied to a conventional recording means, for example a chart recorder (not shown), which produces a graph similar to that shown in FIG. 2b.

The apparatus may, of course, be operated by a technician to obtain data for subsequent use and interpretation by a medically qualified person.

Of course, if it is not required to sense any natural electrical activity of the atrium, then the atrium sense output 56 and therefore the second network 60 and associated circuitry may be omitted.

Figure 6:
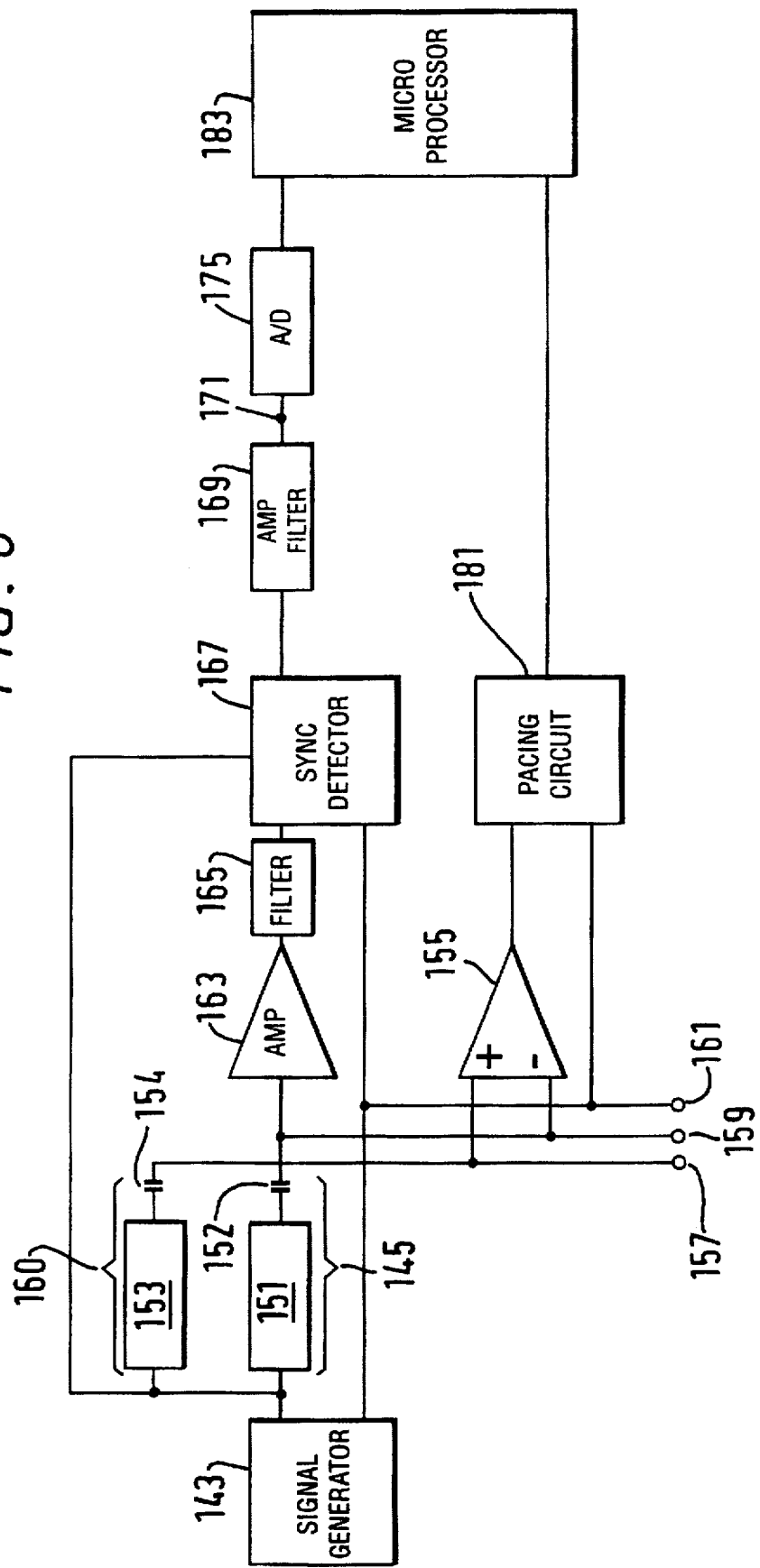
FIG. 6 shows a schematic block diagram of a pacemaker embodying the invention.

FIG. 6, shows schematically a rate responsive pacemaker embodying the invention and controlled on the basis of the transvalvular impedance of the heart.

In FIG. 6 reference numerals that correspond to items of the first embodiment have been retained save that they have been prefixed by the digit "1".

Signal generator 143, first impedance network 145, second impedance network 160, amplifier 163, filter 165, synchronous detector 167, differential amplifier 155, amplifier/filter 169 and connection pins 157, 159 and 161 are the same as those used in the example of FIG. 5 and will not be described further.

In this embodiment, the output 171 of amplifier/filter 169 is supplied via an analogue to digital converter 175 to microprocessor 183, which provides control signals for a rate responsive pacing circuit 181.

Signal generator 143 is preferably pulsed with a low duty cycle square wave so that the alternating voltage waveform is only periodically produced, for example a single cycle of a 4 KHz square wave may be produced once every 25 ms (milliseconds). In this manner the power consumption can be reduced by a factor of 100.

A signal sensed from the sinus node by the atrium electrodes is supplied as an atrium sense signal of a conventional style to the pacing circuit 181 by the differential amplifier 155 to allow pacing of the ventricle to be controlled. Conventional circuitry internal to the pacing circuit 181 determines whether the said atrium signal is sufficient to control pacing although such determination could alternatively be performed by the microprocessor 183. If the natural signal sensed by the atrium electrodes is not sufficient to control pacing, then the microprocessor 183 determines the pacing rate at which the pacing circuit should function from the digital signal supplied by the analogue to digital convertor 175. The microprocessor 183 preferably derives a suitable pacing function using the equation:

$$\text{Pacemaker rate} = R_0 + K_1(T_{CYCLE}/T_1) + K_2(dZ/dT)$$

where $R_0$, $K_1$ and $K_2$ are constants to be programmed into the pacemaker logic circuitry dependent upon individual patient needs, $T_{CYCLE}$, $T_1$ and $dZ/dT$ are as previously defined and are derived by the microprocessor 183 from the impedance measurement signal.

It will, of course, be appreciated by a person skilled in the art that a more complex algorithm could be used in order to account for non-linearities. Alternatively the control could be effected by means of a look-up table in the microprocessor.

Generally, the connection to the ventricle electrode will be such as to cause the pacing circuit 181 not to pace the ventricle if a natural ventricular stimulation is detected. This requires that the pacing circuit 181 be able to detect a natural ventricular stimulation sensed by the ventricle electrode. In order to avoid the signal from the signal generator 43 interfering with the natural ventricular sensed signal, the pacing circuit may be provided with suitable filtering means or may use threshold detection as the signal amplitudes should be a different order. Preferably, however, the microprocessor 183 is programmed to disable sensing of natural ventricular stimulation whilst an impedance measurement is being made.

The above described pacemaker is a so-called VDD pacemaker in which any natural electrical activity in both the atrium and the ventricle is sensed but only the ventricle is paced. The present invention could, however, also be applied to pacemakers in which both the atrium and the ventricle are paced, that is so-called DDD pacemakers which generally require the use of two electro-catheters the first having two electrodes in the atrium and the second having two in the ventricle. In such a case, the impedance measurement is preferably made between the floating atrial and ventricular electrodes (rather than the fixed electrodes used to apply pacing signals to the heart) because the growth of scar tissue around the fixed electrode means that they are no longer directly in contact with the blood in the heart and so would not provide as accurate a means of measurement of the impedance across the tricuspid valve. Also, for the reason given above, it is preferable to make the measurement of the impedance between the atrial and ventricular electrodes closest to tricuspid valve.

Of course, in the case where two electrodes are provided in the ventricle, output from the two ventricular electrodes may be supplied to a differential amplifier to remove the impedance measuring signal in a similar manner to that described above for the atrium sense signal.

The impedance measurement may also be used to control a number of other (optional) functions in a pacemaker, preferably under microprocessor control because measurement of the impedance across the tricuspid valve allows the mechanical state of the heart to be easily detected.

For example, the results of an impedance measurement may be used to control switching between sinus node triggered and fixed (or rate responsive) pacing in a patient having a pacemaker of the type shown in FIG. 6.

The maximum $Z_{MAX}$ and minimum $Z_{MIN}$ typical impedance values across the tricuspid valve of the patient are first measured to provide reference values where maximum impedance $Z_{MAX}$ is indicative that the tricuspid valve is closed and minimum impedance $Z_{MIN}$ that the tricuspid valve is open. An admissible range ($Z_{MAX} \pm \Delta Z_{MAX}$, $Z_{MIN} \pm \Delta Z_{MIN}$) is thereafter determined. These steps may be performed at implant of the pacemaker or, possibly, post implant by telemetric means. The patient may be asked to perform specific manoeuvres (eg. deep inhalation) to assist in this determination. It may be preferable to make (or confirm) these measurements a few months after implant of the pacemaker because scar tissue may grow around the electrodes in contact with the wall of the heart and so alter the impedance. These reference values and ranges are stored in the microprocessor memory.

Figure 7:
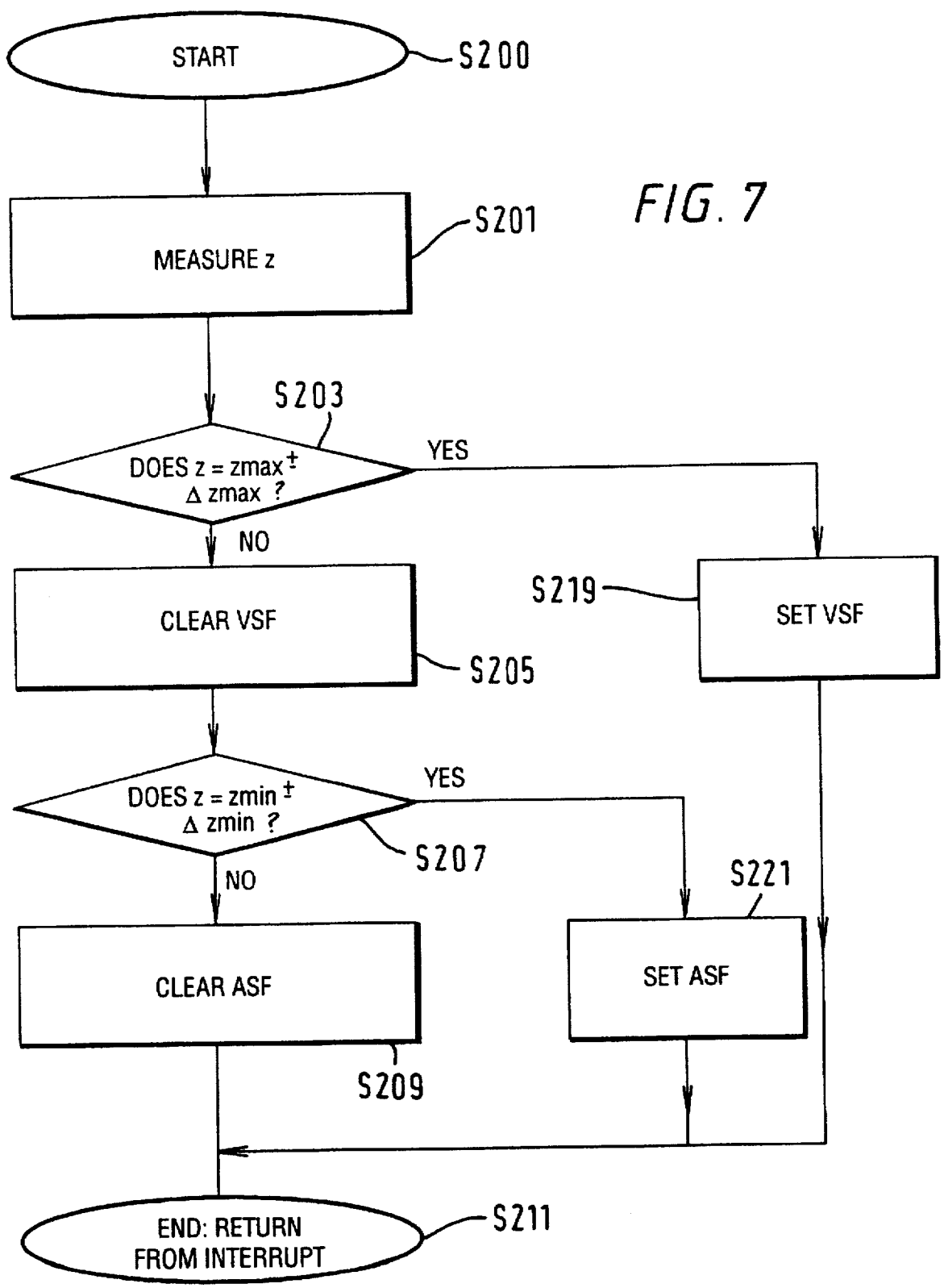
FIG. 7 is a flow chart for illustrating a portion of the software to be implemented in a microprocessor of a pacemaker embodying the invention.

FIG. 7 shows a flow chart illustrating the operation of the microprocessor 183 to set internal flags indicative of the status of the two chambers of the right hand side of the heart.

The process is initiated by a microprocessor interrupt at step S200, the interrupt being provided periodically at a period determined in relation to the signal generator 143 and thus the impedance measuring interval. The microprocessor then reads at step S201 the signal from Analogue to Digital converter 175. In step S203 the microprocessor assesses whether that input data falls within the range $Z_{MAX} \mp \Delta Z_{MAX}$ and, if so determines that the tricuspid valve is closed and that there is ventricular contraction and so sets a ventricular systole flag VSF at step S219. In the event that the impedance measurement is not within such a range the microprocessor clears VSF at step S205 and then determines whether there the measured impedance is within the range $Z_{MIN} \mp \Delta Z_{MIN}$. If so, the microprocessor determines that the tricuspid valve is open and that thus the ventricular filling phase and atrial contraction are occurring and so sets an atrial systole flag ASF (step S221). If the impedance is not within the above range ASF is cleared by step S209. In either event the program is thereafter terminated, that is to say it returns from the interrupt. It will be apparent to the person skilled in the art that the initiation of the above program need not be on the basis of a time periodic interrupt, but could, for example, be triggered by a "data ready" indication from Analogue to Digital converter 175.

The two flags VSF and ASF may be used by the microprocessor 183 for mode switching of the pacing circuit 181, that is to say for controlling switching between a mode where pacing is triggered by activity detected in the sinus node and a mode where rate responsive pacemaker controlled pacing must be performed because such activity is insufficient, inactive or erroneous.

Figure 8:
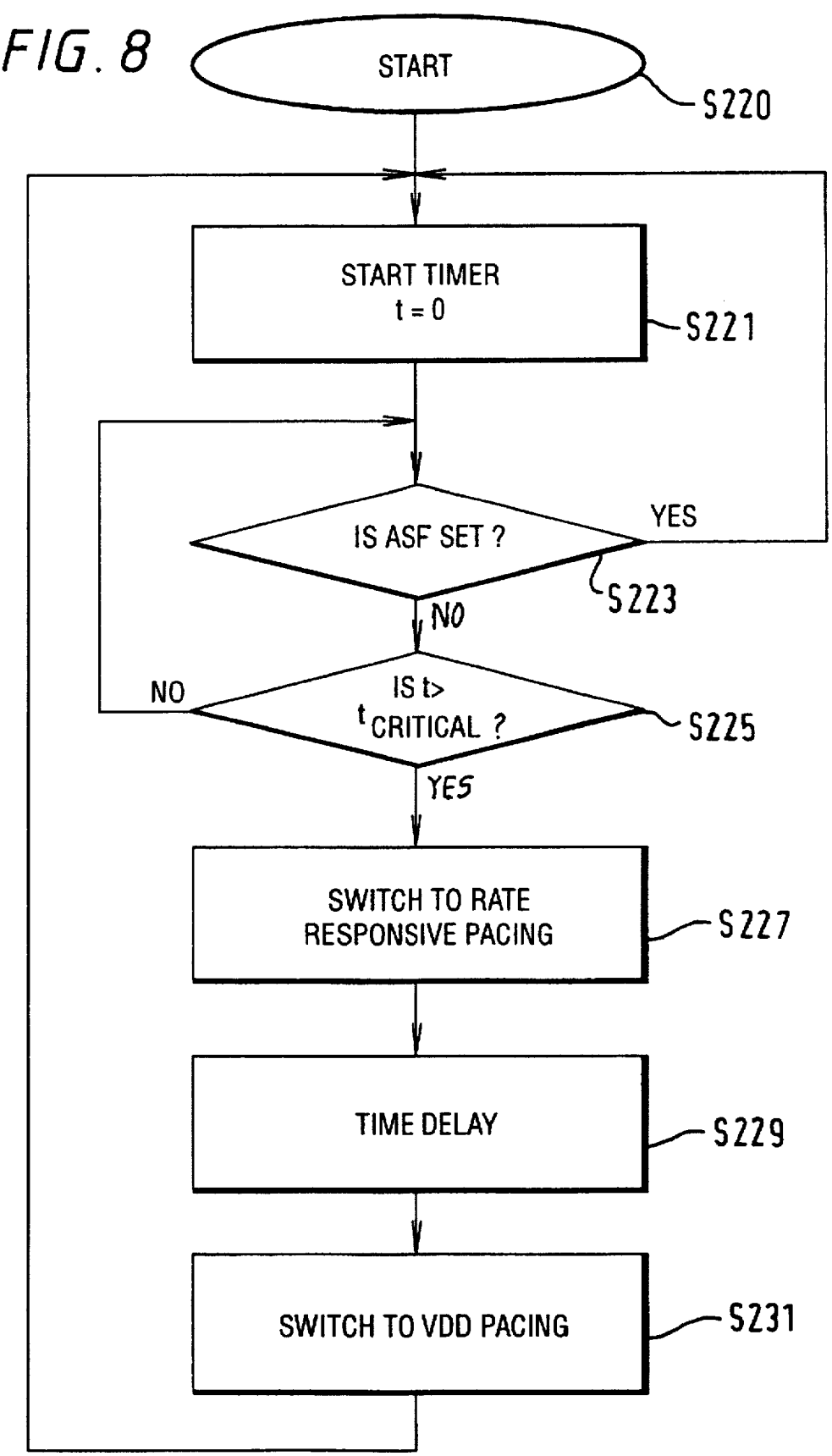
FIG. 8 is a flow diagram for illustrating a portion of the software to be implemented in a pacemaker embodying the invention.

FIG. 8 shows one example of a mode switching algorithm. Pacing is initially performed in VDD mode (step S220) as described above. In step S221 an internal microprocessor timer is started. Thereafter in step S223 the status of the internal flag ASF controlled by the routine of FIG. 7 is examined. If this flag is set this indicates that an atrial systole has occurred and the microprocessor returns to step S221. If ASF is not set, the microprocessor assesses at step S225 whether the time period in which no such flag has been set is in excess of a critical time $T_{critical}$ since the last time ASF was set. If $T_{critical}$ has not been exceeded the program returns to step S223, that is to say, continues checking whether ASF is set (step S223). If the critical time has been exceeded without the detection of ASF, this indicates that an atrial standstill or fibrillation condition has occurred and the microprocessor then causes the pacing circuit to switch to rate response pacing mode, at step S227. This type of pacing is conventionally referred to as $VVI_{rr}$, that is to say ventricular stimulation is carried at a rate responsive frequency, but is inhibited when a natural ventricular signal is sensed.

Once rate responsive pacing has been selected it may be desirable periodically to confirm that such pacing is still a necessity. This confirmation may be carried out by, after a time delay at step S229, temporarily switching to VDD operation in step 231 and checking whether an ASF is set within $t_{critical}$ by repeating steps S221 to S225. It will be apparent that the time delay at S229 should be in excess of a number of heartbeat cycles and may be adjusted dependant upon the propensity of the patient to need rate responsive pacing.

As will be apparent to one skilled in the art that in the second mode described above the pacemaker need not be rate-responsive but could pace at a fixed rate (conventionally termed VVI, that is to say ventricular pacing at a fixed frequency inhibited by ventricular sensing).

It will yet further be apparent that switching between any natural rate pacing and artificial rate pacing modes could be performed by suitable modification of the above described arrangement. In particular DDD pacing could be switched to DDI, that is pacing with atrial stimulation inhibited by atrial sensing, synchronised ventricle stimulation inhibited by ventricular sensing both stimulations being performed at a basic rate or rate responsive DDI ($DDI_{rr}$).

As another possibility the intensity of stimulus provided by the pacemaker may be automatically reduced by use of the measured impedance to the minimum necessary to provoke stimulation (within a suitable safety margin) in order to prolong the battery life and thus extend the time between replacements of the implanted device. This may be achieved using apparatus consisting of a VDD pacemaker system comprising the impedance measuring device of FIG. 6 and the electro-catheter of FIG. 3 save that the pacing circuit 181 should be adapted in order that the voltage of stimulation (hereinafter referred to as the intensity of stimulation) can be adjusted under the control of the microprocessor 181. The interrupt driven routine shown in FIG. 7 hereof may again be used to provide flags VSF and ASF, although only the flag VSF need be provided.

In this case, if, within a (programmable) interval after an attempt to artificially stimulate the ventricle, a corresponding VSF is detected, this is indicative that the applied stimulus is (at least) sufficient. The microprocessor may be programmed to then reduce the stimulus voltage to a stage where, within a suitable safety margin, the stimulus voltage is just sufficient to stimulate the heart. It will, of course, be appreciated that the lack of a corresponding VSF after attempted ventricle stimulation will be indicative of the stimulation intensity being too low. The microprocessor 183 can therefore command that the chamber be restimulated at a higher intensity and also that the stimulus intensity is upwardly adjusted. Such stimulus intensity adjustment is not limited to VDD pacing but could be used in other pacing modes such as DDD pacing. In such a case the intensity of atrium stimulation may be similarly adjusted under microprocessor control.

Figure 9:
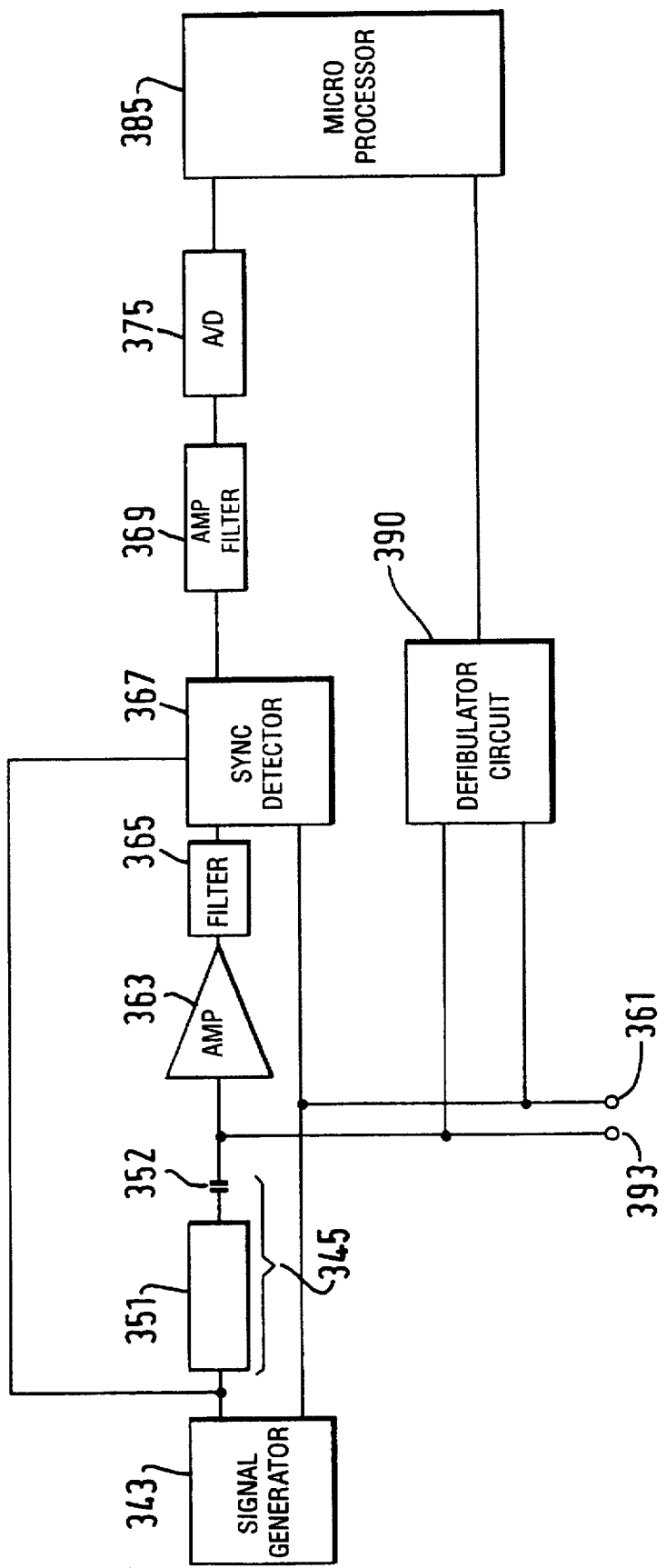
FIG. 9 shows a schematic block diagram of a defibrillator embodying the invention.

FIG. 9 shows apparatus suitable for an implantable defibrillator. Items that correspond to the embodiment of FIG. 6 are given the same reference numerals as that embodiment save that they are prefixed by FIG. "3" rather than FIG. "1".

In this example an implantable defibrillator lead (commonly available) is used instead of pacing lead 17. This lead has only two electrodes one placed in the atrium and one placed in the ventricle. These electrodes are significantly larger in size than those of a pacemaker lead because, the object of a defibrillator is to deliver a proportionally very large electric voltage to the heart in order to restart it from a fibrillation condition.

Signal generator 343, network 345, amplifier 363, filter 365, synchronous detector 367, amplifier/filter 369, analogue-to-digital converter 375, microprocessor 383, and ventricle connection pin 361 are the same as those shown in FIG. 6. However, only a single atrium connection 393 is required and thus the second impedance network 160 is omitted.

Defibrillator circuit 390 effectively replaces pacing circuit 181. The defibrillator circuit is under the control of microprocessor 383.

In this embodiment the interrupt initiated routine of FIG. 7 is again used except that the microprocessor only monitors flag VSF and so the parts of that routine relating the setting and clearing of ASF are omitted. If the VSF flag is not set a predetermined time period, typically 5 seconds, set at implant of the defibrillator then a ventricular standstill or fibrillation is indicated. In the event of ventricular standstill or fibrillation, the defibrillator is triggered.

It will be apparent to one skilled in the art that the provision of a parameter indicative of the mechanical state of the heart has a wide number of uses in implantable devices and such conventional devices could be easily adopted to make use of such a parameter. Yet further means could be placed in such a device to allow the information to be read externally (e.g. by telemetric linkage) without the need to remove the implantable device.

Also, an impedance measurement made in the manner described above with reference to, for example, FIG. 1, may also be used to monitor the operation of the heart of a human or animal to enable information about the mechanical operation to be collected for use in subsequent testing or diagnostic proceedings to determine whether the heart is functioning correctly.

Figure 10:
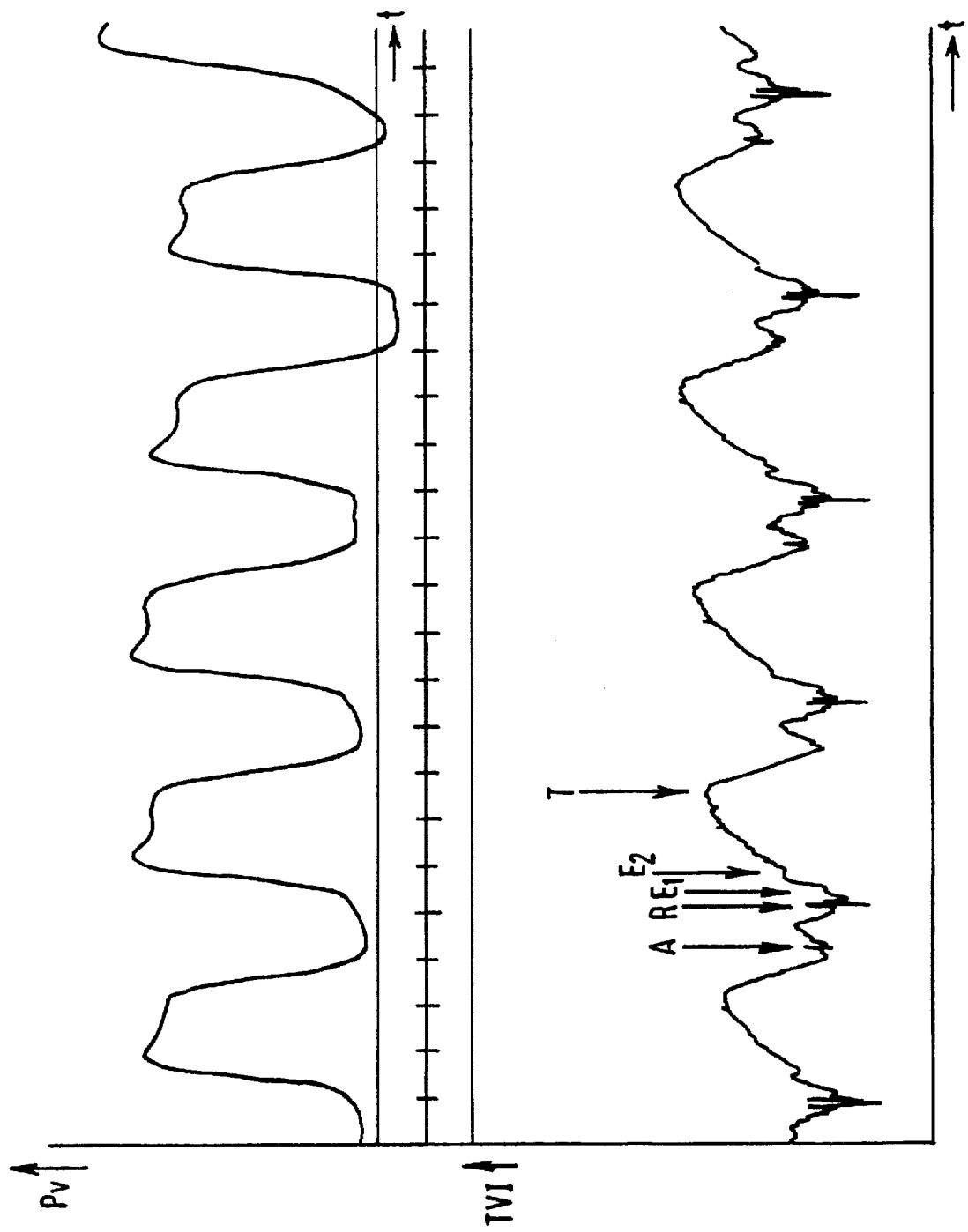
FIG. 10 shows sample output, obtained during pre-clinical trials on pigs, from a ventricular blood pressure sensor and an impedance measuring apparatus according to the invention.
Figure 11:
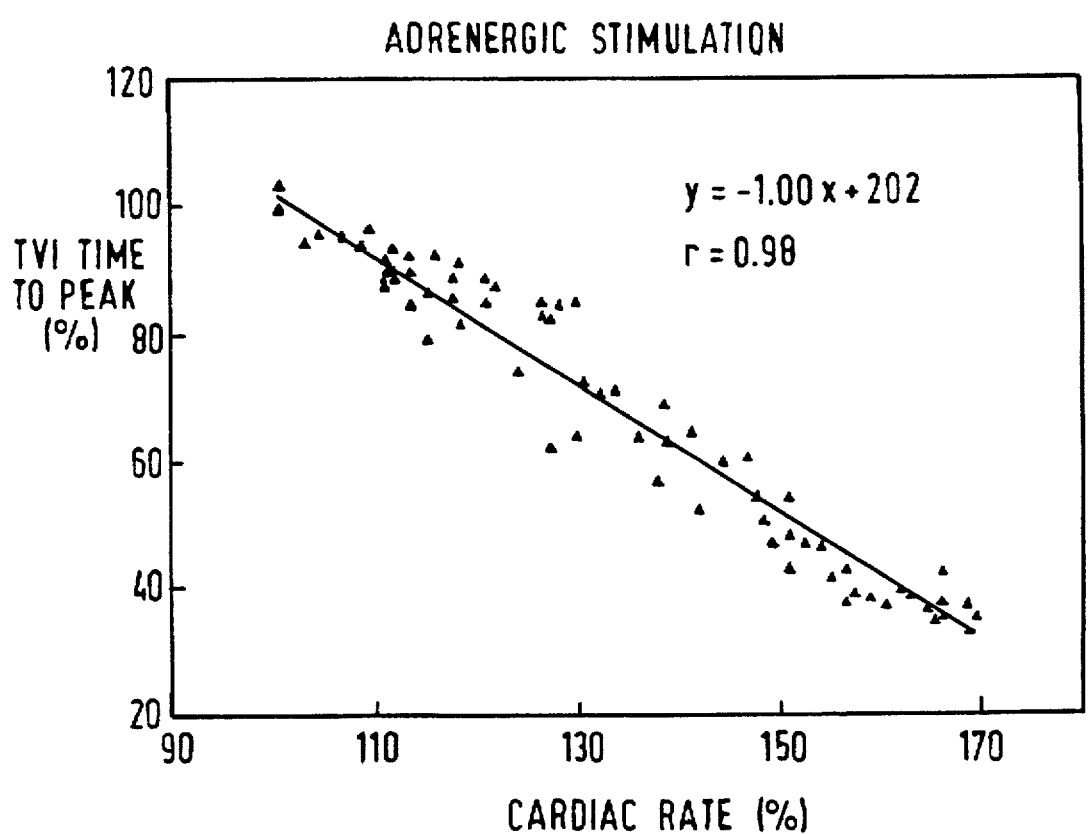
FIG. 11 shows a graph produced after processing of impedance results produced by a measuring device according to the invention obtained during pre-clinical trials on pigs.

FIGS. 10 and 11 show results obtained during pre-clinical experiments using an embodiment of the invention, such as that shown in FIG. 5 when connected to a chart recorder.

In these experiments a catheter was implanted into pigs weighing between 20 and 40 kilograms. These pigs were under general anaesthesia by NA-pentobarbital and artificial ventilation. A type 830-S single pass catheter lead, adapted to the size of the animal (atrial inter-electrode distance 15 mm, atrium-ventricle inter-electrode distance 50–60 mm) was inserted into the right hand chambers of the heart through the jugular under fluoroscopic control. Additionally right ventricular pressure and aortic pressure were simultaneously measured using a pressure transducer such as the Millar micro-tip pressure transducer. The output signal of the embodiment together with an external electrocardiograph were recorded on paper using a chart recorder such as the Gould 6-channel polygraph and additionally onto a storage medium to allow subsequent digitisation and analysis.

FIG. 10 shows a paradigm of the change of the transvalvular impedance signal ($TV_1$) (lower trace) against time (t) derived by a measurement device according to the invention in pigs during resting sinus rhythm. The upper trace shows ventricular pressure ($P_v$) on the same time axis. Various events during the cycle are marked by reference arrows. In a typical cycle the ECG detected A-wave signal which corresponds to atrium contraction is shown in the impedance measurement signal by a slight rise in transvalvular impedance which the inventor attributes to the reduction in volume of blood in the lower part of the atrium. The transvalvular impedance thereafter decreases until the time of the ECG detected R-wave which corresponds to the time of ventricular filling. Indicated event $E_1$ corresponds to an initial fast increase in transvalvular impedance followed by indicated event $E_2$ which corresponds slower increase in transvalvular impedance. These rises in transvalvular impedance are attributed to ventricular systole. The slower transvalvular impedance increase concludes when maximum aortic pressure is reached, at the same time as which the T-wave is detected by the surface ECG. Thereafter the ventricular pressure drops during ventricular relaxation reaching a minimum during fast ventricular filling (at which time the A-wave is detected). It will thus be seen, that there is a high correlation between events detectable by the transvalvular impedance measurement and those indicated by the surface ECG.

FIG. 11 is a graph showing the transvalvular impedance rise time (from minimum to maximum) ($T_1$) as a percentage of the mean based value against the cardiac rate as a percentage of a basic (rest) heart rate. The results pool two consecutive trials in which cardiac rate was increased in the pigs by the administration of adrenalin with a dose of 1.25 micrograms/kilogram and 2.5 micrograms/kilogram, respectively. It will be seen from the figure that a very high correlation between these two quantities was observed and thus the time period $T_1$ should provide a good indication within a human patient of the necessary cardiac rate and so of the rate at which a rate responsive pacemaker should be operated.

Figure 12:
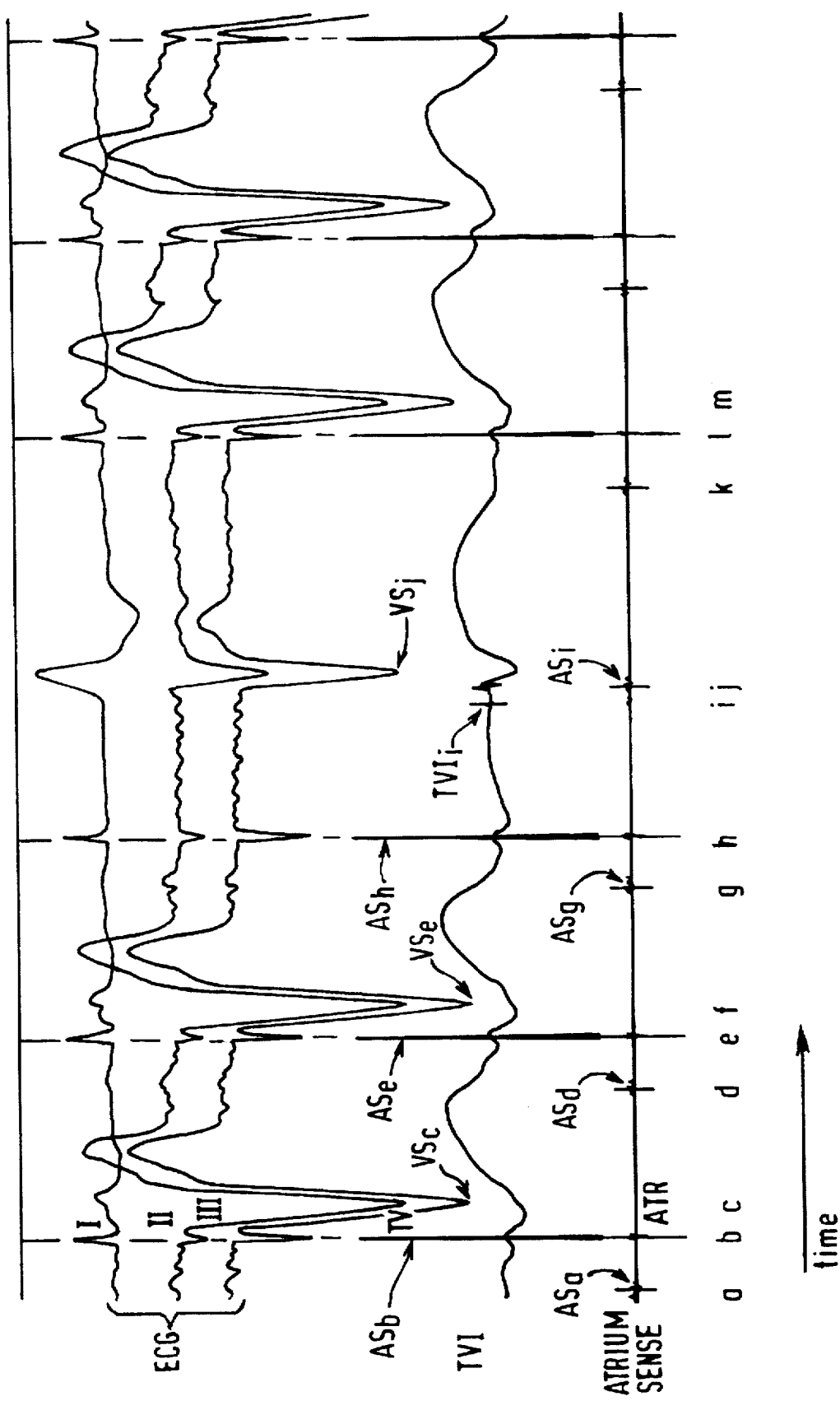
FIG. 12 shows electrocardiograph, atrium sense and transvalvular impedance measurements obtained from a patient.

FIG. 12 shows the results of a clinical trial of using apparatus embodying the present invention to monitor the transvalvular impedance. The patient had been previously been fitted with a conventional VDD pacemaker and the transvalvular impedance measuring device was fitted so as to make use of the same catheter. The results were recorded in a patient undergoing a pacemaker replacement for physiologic battery depletion. During this operation, the patient was temporarily fitted with a further pacing lead, the electrode of which was placed in the septal region. Three sets of traces are indicated on the figure. The upper trace is a conventional surface ECG and itself consists of three distinct traces I, II and III. The centre trace in the figure shows the change with time (t) of the transvalvular impedance measurement TVI produced by apparatus embodying the invention. The lower trace shows the change with time (t) of the output AS of the atrium sensing electrode of the catheter, a single atrium electrode lead being installed in this patient.

At time a the natural atrium stimulation signal $AS_a$ is produced. The pacemaker fitted to this patient will thereafter produce a ventricle stimulus and this is detected as shown at $AS_b$ by the atrium sensor electrode (time event b)

It will thereafter be seen (event c) that a ventricular systole is successfully stimulated and this is detected both by the surface ECG as blip VSc and by an increase in the transvalvular impedance measurement.

Events d, e and f in the following cardiac cycle correspond to events a, b and c. However, in the next cardiac cycle, despite there being a detected atrium stimulus $AS_g$ (event g) and the pacemaker producing a ventricle stimulus detected as $AS_h$ (event h), no ventricle systole actually occurs and there is no blip or trough in the ECG trace III corresponding to $VS_c$ or $VS_e$. Similarly, the expected increase in the transvalvular impedance TVI does not occur. In this case, because no ventricle systole occurred, an additional stimulus was applied to the electrode inserted in the septal region at time event i. This effect stimulus is shown on the diagram by a small blip in transvalvular impedance and a very slight change $AS_i$ in the atrium sense output (event i). This additional electrode successfully triggers a ventricle systole (event J) and this is detected both by the ECG at $VS_j$ and by increase in the transvalvular impedance measurement. Subsequently the cardiac cycle returns to normal as shown by events k, l and m.

It will therefore be seen, that the measurement of transvalvular impedance is successful in detecting where a stimulation has been unsuccessful in causing a ventricular systole. This measurement may, therefore, be usefully employed in a conventional pacemaker in order that a further (preferably increased) electrical stimulus be applied to the ventricle.

The transvalvular impedance thus provides a useful indication of the mechanical status of the heart which has a number of applications in pacemakers and implantable defibrillators. The precise use to which the measurement is put in any particular patient will be dependent upon the type of pacemaker or defibrillator and the particular heart defects suffered by the patient. A single device could be implanted and could be programmed differently depending upon the patient's needs. Instructions suitable for the control of a microprocessor-controlled pacemaker may be stored, for example, on removable storage media which could then be transferred to a storage medium internal to the implantable device. Such transfer could occur in a wireless form in order to remove the necessity of conducting an operation to remove or expose the implantable device.

Other variations and modifications will be apparent to those skilled in the art.

What is claimed is:

1. An apparatus for providing a signal indicative of a mechanical function of a heart, the apparatus comprising:
   means for connection to an atrium electrode arranged to be placed in the atrium of one side of the heart;
   means for connection to a ventricle electrode arranged to be placed in the ventricle of said one side of the heart;
   means for sensing an impedance between the atrium electrode connection means and the ventricle electrode connection means; and
   means for deriving a measurement of the impedance across the valve between the atrium and the ventricle of said heart from said sensed impedance.

2. An apparatus according to claim 1, wherein the impedance measuring means is adapted to make a plurality of impedance measurements, the impedance measuring means further comprising processing means for processing the measurements in order to provide at least one of the following:
   an impedance measurement cycle time indicative of the beat rate of the heart;
   the time of occurrence of an impedance minimum as indicative of the time at which the valve between the atrium and the ventricle is open;
   the time of occurrence of an impedance maximum as an output signal indicative of the time at which the valve between the atrium and the ventricle is closed; and
   the time between an impedance minimum and the following impedance maximum as an output signal indicative of the time taken for the valve between the atrium and the ventricle to close.

3. An apparatus according to claim 1, wherein the impedance sensing means comprises means for periodically measuring the impedance.

4. An apparatus according to claim 3, wherein the periodic measuring means comprises signal generating means for periodically applying a measuring signal to at least one of the electrodes.

5. An apparatus according to claim 3, wherein the impedance sensing means comprises means for comparing the voltage across a known impedance with the voltage between the two electrodes.

6. An apparatus according to claim 1 further comprising heart stimulating means for providing an electrical stimulus to a chamber of the heart at least partly on the basis of an output of the impedance deriving means.

7. An apparatus according to claim 6, wherein said heart stimulating means is adapted to stimulate a chamber of the heart at a predetermined basic rate, and comprises means for modifying the rate on the basis of an output of the impedance deriving means.

8. An apparatus according to claim 6, further comprising an electro-catheter provided with at least one atrium and one ventricle electrode for receiving signals from and supplying signals to the heart stimulating means, the atrium electrode of the electro-catheter being connected to the atrium electrode connection means and the ventricle electrode of the electro-catheter being connected to the ventricle electrode connection means.

9. An apparatus for providing a signal indicative of a mechanical function of a heart, the apparatus comprising:
   an electro-catheter for insertion into the heart, the electro-catheter having an atrium electrode adapted so as to float, in the atrium chamber of the heart and a corresponding ventricle electrode; and
   means for measuring the impedance between the floating atrium electrode and the ventricle electrode.

10. An apparatus according to claim 9, wherein the impedance measuring means is adapted to make a plurality of impedance measurements, the impedance measuring means further comprising processing means for processing the measurements in order to provide at least one of the following:
    an impedance measurement cycle time indicative of the beat rate of the heart;
    the time of occurrence of an impedance minimum as indicative of the time at which the valve between the atrium and the ventricle is open;
    the time of occurrence of an impedance maximum as an output signal indicative of the time at which the valve between the atrium and the ventricle is closed; and
    the time between an impedance minimum and the following impedance maximum as an output signal indicative of the time taken for the valve between the atrium and the ventricle to close.

11. An apparatus according to claim 9, wherein the impedance measuring means comprises means for periodically measuring the impedance.

12. An apparatus according to claim 11, wherein the periodic measuring means comprises signal generating means for periodically applying a measuring signal to at least one of the electrodes.

13. An apparatus according to claim 11, wherein the impedance measuring means comprises means for comparing the voltage across a known impedance with the voltage between the two electrodes.

14. An apparatus for controlling an operation of the heart the apparatus being suitable for connection to an electro-catheter having at least one atrium electrode adapted to be placed in a floating position in an atrium and at least one ventricle electrode for placing in the corresponding ventricle of a heart, the apparatus comprising:
    stimulating means for receiving signals from the atrium electrode and supplying signals to the ventricle electrode to stimulate operation of the heart;
    means for sensing an impedance between the atrial and the ventricle electrode;
    means for deriving a measurement of the impedance across the valve between the atrium and the ventricle of said heart from said sensed impedance; and
    control means for controlling supply of signals from the stimulating means to the ventricle electrode in accordance with an output signal supplied by the impedance deriving means.

15. An apparatus according to claim 14, wherein the impedance measuring means is adapted to make a plurality of impedance measurements, and further comprises processing means for processing the measurements in order to provide at least one of the following:
    an impedance measurement cycle time indicative of the beat rate of the heart;
    the time of occurrence of an impedance minimum as indicative of the time at which the valve between the atrium and the ventricle is open;

the time of occurrence of an impedance maximum as an output signal indicative of the time at which the valve between the atrium and the ventricle is closed; and the time between an impedance minimum and the following impedance maximum as an output signal indicative of the time taken for the valve between the atrium and the ventricle to close.

16. An apparatus according to claim 15, wherein the stimulating means comprises a pacing unit.

17. An apparatus according to claim 16, wherein a rate of pacing is determined at least partly on the basis of the output signal from the impedance deriving means.

18. An apparatus according to claim 15, wherein stimulating means comprises a defibrillation unit.

19. An apparatus according to claim 18, wherein the control means is adapted to cause the defibrillation unit to supply a defibrillation signal to the ventricular electrode when a signal representing a predetermined maximum impedance indicative of closure of the valve between the atrium and the ventricle is not received within a predetermined time.

20. An apparatus according to claim 14, wherein at least two atrial electrodes are provided and further comprising means for deriving an atrial sense signal indicative of the natural electrical activity of the atrium from the difference between signals supplied by the two atrial electrodes.

21. An apparatus according to claim 14, wherein the impedance measuring means comprises means for supplying a pulsed or alternating measurement signal to at least one of the electrodes.

22. A control circuit comprising transvalvular impedance measurement means adapted to provide an indication of a mechanical function of a heart.

23. A control circuit according to claim 22 adapted for the control of a pacemaker or implanted defibrillator.

24. A control circuit according to claim 22 further comprising processing means for processing the measurements in order to provide at least one of the following:

an impedance measurement cycle time indicative of the beat rate of the heart;

the time of occurrence of an impedance minimum as indicative of the time at which the valve between the atrium and the ventricle is open;

the time of occurrence of an impedance maximum as an output signal indicative of the time at which the valve between the atrium and the ventricle is closed; and the time between an impedance minimum and the following impedance maximum as an output signal indicative of the time taken for the valve between the atrium and the ventricle to close.

25. A method of providing a signal indicative of the operation of a heart by measuring an impedance between electrodes provided on either side of the valve separating the atrium and ventricle chambers of one side of the heart wherein at least one of said electrodes is adapted so as not to contact with a wall of the heart.

26. A method according to claim 25, which comprises determining at least one of the following:

the manner in which the measured impedance changes with time to determine information about the operation of the heart;

a cycle time of the measured impedance to determine information relating to the beat rate of the heart;

the maximum value of the measured impedance during a cycle to determine information relating to valve closure;

the maximum value of the measured impedance during a cycle to determine information relating to valve opening;

and the rate of change of impedance between a minimum value and the subsequent maximum value in a cycle to determine information relating to the contractivity of the heart.

27. A method of operating a heart stimulating device, which method comprises measuring an impedance between electrodes provided on either side of the valve separating the atrium and ventricle chambers of one side of the heart, at least one of said electrodes floating in the chamber of the heart and using the measured impedance to control operation of the heart stimulating device, so as to control at least one of the intensity of stimulation provided by the heart stimulating device; a signal of the heart stimulating device which controls the heart beat rate; or stimulation of ventricular activity of the heart when a predetermined maximum value of the measured impedance is not measured within a predetermined time.

28. Apparatus for controlling operation of a heart pacing unit, comprising means for measuring the impedance across a valve between an atrium and ventricle of a heart and means for determining a pacing rate for a heart pacing circuit in accordance with the following equation:

pacing rate=$R_0 + K_1(T_{CYCLE}/T_1) + K_2(dZ/dT)$ where $R_0$, $K_1$ and $K_2$ are determined by the characteristics of the heart to be paced, $T_{CYCLE}$ is the period of cyclical variation of the transvalvular impedance signal, $T_1$ is the time between an impedance minimum and maximum, and $dZ/dT$ is the rate of change of the transvalvular impedance between the minimum and maximum.

29. An apparatus for providing a signal indicative of a mechanical function of a heart, the apparatus comprising:

means for connection to an atrium electrode of an electro-catheter;

means for connection to a ventricle electrode of an electro-catheter; and means for measuring the impedance between the atrium electrode connection means and the ventricle electrode connection means;

wherein the impedance measuring means comprises means for periodically measuring the impedance and for comparing the voltage across a known impedance with the voltage between the two electrodes.

30. An apparatus for providing a signal indicative of a mechanical function of a heart, the apparatus comprising:

an electrocatheter for insertion into the heart, the electro-catheter having an atrium electrode and a ventricle electrode; and means for measuring the impedance between the atrium electrode and the ventricle electrode;

wherein the impedance measuring means comprises means for periodically measuring the impedance and means for comparing the voltage across a known impedance with the voltage between the two electrodes.

31. An apparatus for controlling an operation of the heart the apparatus being suitable for connection to an electro-catheter having at least one atrial electrode for placing in an atrium and at least one ventricle electrode for placing in a ventricle of a heart, the apparatus comprising:

defibrillation means for receiving signals from the atrial electrode and supplying signals to the ventricle electrode to stimulate operation of the heart;

impedance measuring means for periodically measuring an impedance between the atrial and the ventricle electrode;

control means for controlling supply of signals from the defibrillation means to the ventricle electrode in accordance with an output signal supplied by the impedance measuring means; and processing means for processing the impedance measurements in order to provide the time of occurrence of an impedance maximum as an output signal indicative of the time at which the valve between the atrium and the ventricle is closed;

wherein the control means is adapted to cause the defibrillation unit to supply a defibrillation signal to the ventricular electrode when a signal representing a predetermined maximum impedance indicative of closure of the valve between the atrium and the ventricle is not received within a predetermined time.

32. An apparatus for controlling an operation of the heart the apparatus being suitable for connection to an electro-catheter having at least one atrium electrode for placing in an atrium and at least one ventricle electrode for placing in a ventricle of a heart, the apparatus comprising:

stimulating means for receiving signals from the atrium electrode and supplying signals to the ventricle electrode to stimulate operation of the heart;

impedance measuring means for measuring an impedance between the atrium and the ventricle electrode; and means for controlling supply of signals from the stimulating means to the ventricle electrode in accordance with an output signal supplied by the impedance measuring means;

wherein at least two atrium electrodes are provided and means are provided for deriving an atrial sense signal indicative of the natural electrical activity of the atrium from the difference between signals supplied by the two atrial electrodes.

33. An apparatus for providing a signal indicative of a mechanical function of a heart and a signal indicative of the electrical activity of the heart using an electro-catheter having first and second atrium electrodes, the first atrium electrode being adapted so as to float in the atrium chamber and a ventricle electrode, the apparatus comprising:

impedance measurement means for measuring the transvalvular impedance between the first atrium electrode and the ventricle electrode so as to produce said signal indicative of the mechanical state of the heart;

a differential amplifier for receiving signals from the first and the second atrium electrodes and for outputting a signal of the difference therebetween, said signal being indicative of the electrical activity of the heart;

wherein the impedance measurement means comprises first and second impedances of equal values having first ends coupled together, a second end of the first impedance being arranged to be coupled to the first atrium electrode to form a potential divider with the transvalvular impedance to be measured whereby in use a voltage across the first atrium and ventricle electrode is indicative of the transvalvular impedance, and a second end of the second impedance being arranged to be coupled to the second atrium electrode for providing the same signals to the first and second atrium electrodes so that the output of the differential amplifier is not influenced by the transvalvular impedance measurement.

* * * * *